(12) United States Patent
Kawaura et al.

(10) Patent No.: US 10,722,691 B2
(45) Date of Patent: Jul. 28, 2020

(54) PUNCTURE APPARATUS

(71) Applicant: TERUMO KABUSHIKI KAISHA, Tokyo (JP)

(72) Inventors: Masakatsu Kawaura, Sunnyvale, CA (US); Nao Mandai, Mountain View, CA (US); Nobuo Takahashi, Cupertino, CA (US); Thomas J. Fogarty, Portola Valley, CA (US); David Willis, Los Altos, CA (US); Thomas Howell, San Jose, CA (US); Peter Carlotto, San Jose, CA (US); Shuji Uemura, San Francisco, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 472 days.

(21) Appl. No.: 15/156,747

(22) Filed: May 17, 2016

(65) Prior Publication Data

US 2017/0014218 A1 Jan. 19, 2017
US 2020/0000569 A9 Jan. 2, 2020

Related U.S. Application Data

(60) Provisional application No. 62/192,225, filed on Jul. 14, 2015.

(51) Int. Cl.
*A61M 25/10* (2013.01)
*A61B 17/34* (2006.01)
(Continued)

(52) U.S. Cl.
CPC ......... *A61M 25/10* (2013.01); *A61B 17/3403* (2013.01); *A61F 2/0022* (2013.01); *A61B 17/0218* (2013.01); *A61B 17/0482* (2013.01); *A61B 17/0625* (2013.01); *A61B 17/3468* (2013.01); *A61B 17/42* (2013.01); *A61B 2017/00805* (2013.01); *A61B 2017/306* (2013.01); *A61B 2017/3407* (2013.01); *A61B 2017/3486* (2013.01); *A61B 2017/3488* (2013.01); *A61B 2090/035* (2016.02); *A61B 2090/036* (2016.02); *A61B 2090/062* (2016.02); *A61B 2090/0807* (2016.02);
(Continued)

(58) Field of Classification Search
CPC .......... A61B 17/42; A61B 2017/00805; A61B 2017/306; A61B 2017/308; A61B 2017/3405; A61F 2/0022; A61M 2210/1475
See application file for complete search history.

(56) References Cited

U.S. PATENT DOCUMENTS 5,156,618 A * 10/1992 Fiore ...................... A61B 18/00
604/315
6,911,003 B2 6/2005 Anderson et al.
(Continued)

FOREIGN PATENT DOCUMENTS

WO  WO/2014/162429  * 10/2014  ............. A61B 17/00
WO  WO2015052720   *  4/2015

*Primary Examiner* — Thomas McEvoy
(74) *Attorney, Agent, or Firm* — Buchanan Ingersoll & Rooney PC

(57) ABSTRACT

A vaginal insertion portion is disclosed, the vaginal insertion portion including a base portion, a proximal holding portion located on a proximal side of the base portion, and a suction portion located on distal side of the proximal holding portion.

12 Claims, 13 Drawing Sheets

(51) Int. Cl.
*A61F 2/00* (2006.01)
*A61B 17/02* (2006.01)
*A61B 17/30* (2006.01)
*A61B 17/42* (2006.01)
*A61B 17/00* (2006.01)
*A61B 90/00* (2016.01)
*A61B 17/062* (2006.01)
*A61B 17/04* (2006.01)

(52) U.S. Cl.
CPC .... *A61F 2/0045* (2013.01); *A61M 2210/1092* (2013.01); *A61M 2210/1475* (2013.01)

(56) References Cited

U.S. PATENT DOCUMENTS

| | | | |
|---|---|---|---|
| 2012/0016185 A1* | 1/2012 | Sherts | A61B 17/12099 600/37 |
| 2013/0144191 A1* | 6/2013 | Egorov | A61B 5/227 600/591 |
| 2015/0073465 A1 | 3/2015 | Ariura et al. | |
| 2015/0080644 A1 | 3/2015 | Kawaura et al. | |

* cited by examiner

PUNCTURE APPARATUS

CROSS-REFERENCES TO RELATED APPLICATIONS

This application claims priority to U.S. Provisional Patent Application No. 62/192,225 filed on Jul. 14, 2015, the entire content of which is incorporated herein by reference.

TECHNICAL FIELD

The present disclosure relates to a puncture apparatus, and more particularly to an insertion instrument, which includes a vaginal insertion portion (or vaginal stabilizer) and a urethral insertion portion (or urethral stabilizer).

BACKGROUND DISCUSSION

In a patient suffering from urinary incontinence, for example, stress urinary incontinence, urine leakage (involuntary urination) occurs due to an abnormal pressure exerted during a normal exercise or by, for example, laughing, coughing, or sneezing. This can be attributable, for example, to loosening of a pelvic floor muscle, which is a muscle for supporting a urethra, caused by childbirth.

For treatment of urinary incontinence, surgical therapy can be effective. For example, a tape-shaped implant called a "sling" can be placed indwelling in the body to support the urethra (for example, U.S. Pat. No. 6,911,003). In order to put a sling indwelling in the body, an operator incises a vagina with a surgical knife, dissects a biological tissue (living body tissue) between the urethra and the vagina, and provides communication between the exfoliated biological tissue site and an exterior through an obturator foramen by using a puncture needle. Then, in such a state, the sling is placed indwelling in the body.

If a vaginal wall is once incised, however, there can be a fear that the sling might be exposed to an inside of the vagina via a wound caused by the incision. There can also be a fear that complications might occur which can be caused by an infection via the wound. In addition, since the vaginal wall is incised, an invasiveness of the procedure can be rather great and patient burden can be relatively heavy. In addition, there can be a fear that the urethra or the like can be damaged by a surgical knife in the course of the procedure by the operator, and there can be a fear that the operator himself might damage his fingertip by the surgical knife.

Further, when an implant is placed indwelling in a living body, there may arise a case, depending on a length of the implant, where part of the implant can located near the living body surface, such that the patient may experience pain.

SUMMARY

A puncture apparatus is disclosed by which the burden exerted on a patient can be relatively alleviated when an implant is put indwelling in the living body.

A vaginal insertion portion is disclosed, the vaginal insertion portion comprising: a base portion; a proximal holding portion located on a proximal side of the base portion; and a suction portion located on a distal side of the proximal holding portion.

A puncture apparatus is disclosed comprising: an insertion portion that is insertable into a living body, the insertion portion comprising: a urethral insertion portion having an inflatable and deflatable balloon on a distal end of the urethral insertion portion, and a plurality of suction holes at an intermediate portion of the urethral insertion portion; and a vaginal insertion portion, the vaginal insertion portion having a base portion, a proximal holding portion located on a proximal side of the base portion, and a suction portion located on distal side of the proximal holding portion; and a puncture needle that punctures living body tissues between the urethral insertion portion and the vaginal insertion portion in a state in which the insertion portion is inserted into the living body.

A method is disclosed for suctioning a tissue adjacent a first lumen of a living body, comprising: inserting an insertion portion comprising a base portion, a proximal holding portion located on a proximal side of the base portion, and a suction portion located on a distal side of the proximal holding portion into the first lumen; and applying a suction to the suction portion so that the insertion portion fixes the tissue facing the suction portion through the first lumen.

DETAILED DESCRIPTION

Figure 1:
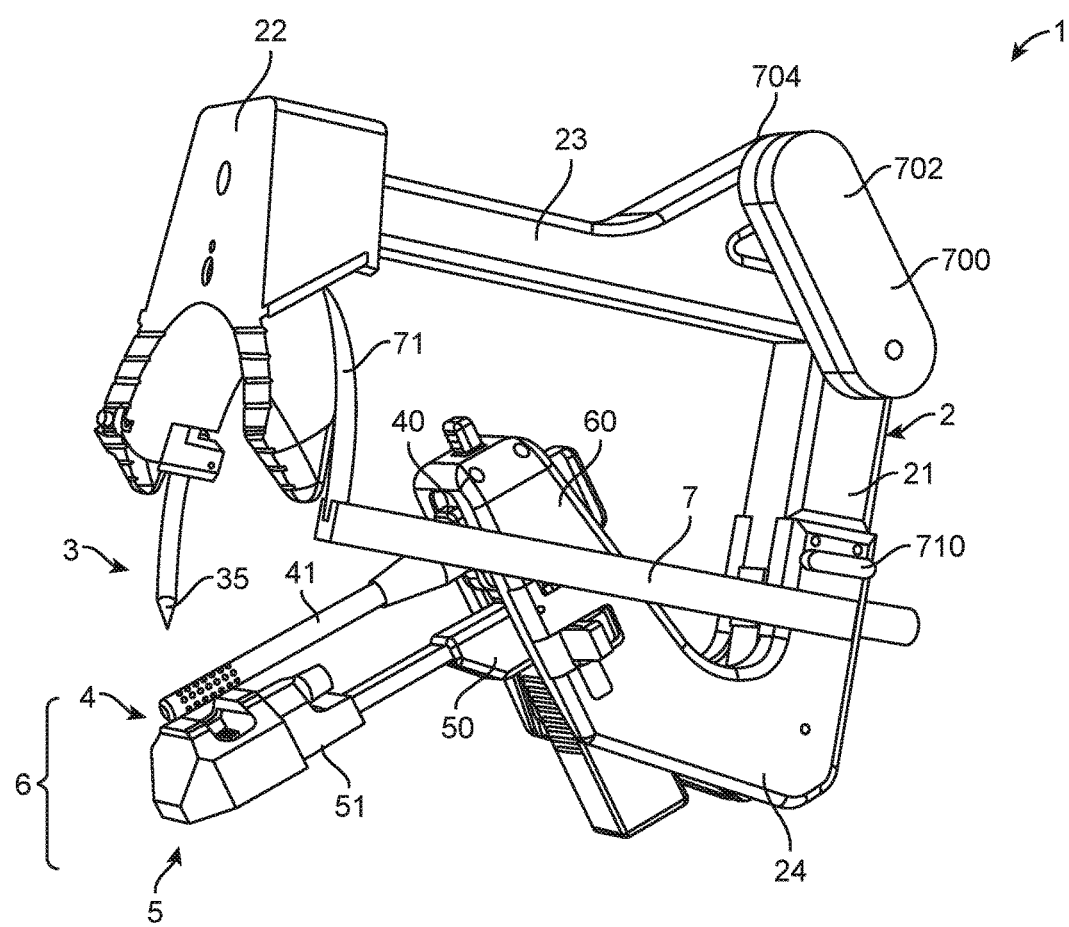
FIG. 1 is a perspective view showing a puncture apparatus to be used at a time of placing indwelling in a living body an implant according to an exemplary embodiment of the present disclosure.

FIGS. 1-14 are views showing a puncture apparatus 1 to be used at a time of placing indwelling in a living body an implant (not shown) according to exemplary embodiments of the present disclosure.

In accordance with an exemplary embodiment, a puncture apparatus 1 as shown in FIGS. 1-5 is an apparatus to be used for treatment of female urinary incontinence, for example, to be used in a process in which a biological tissue-supporting implant for treatment of urinary incontinence is embedded (implanted) into a living body as described in U.S. Patent Publication Nos. 2015/0080644 and 2015/0073465, which are incorporated herein by reference in their entirety.

The puncture apparatus 1 can include a frame (support unit) 2, a puncture member 3, a urethral insertion member 4, a vaginal insertion member 5, and an operating member 7. In the puncture apparatus 1, the urethral insertion member 4 and the vaginal insertion member 5 constitute an insertion instrument 6. The operating member 7 is a member operating the puncture member 3.

Such an operating member 7, as shown in FIGS. 1 to 5, can include an insertion portion 71, which is a portion to be inserted in the puncture member 3, and can function as a stylet that supports the puncture member 3 from the inside. With the insertion portion 71 inserted in the puncture member 3, the puncture member 3 is connected to the operating member 7, whereby it is enabled to operate the puncture member 3 by the operating member 7. Such an insertion portion 71 is in an arcuate shape corresponding to the shape of the puncture member 3. A center angle of the insertion portion 71 is set in conformity with a center angle of the puncture member 3. In accordance with an exemplary embodiment, a distal portion of the insertion portion 71 can be tapered off. The presence of the tapered distal portion can enable relatively smooth fitting of the puncture member 3 over the insertion portion 71 (smooth insertion of the insertion portion 71 into the puncture member 3).

In accordance with an exemplary embodiment, the insertion portion 71 can be circular in cross-sectional shape. Alternatively, the insertion portion 71 may be flat-shaped in cross section. The flat shape is not limited. Examples of the flat shape applicable here can include not only ellipses but also rounded-cornered rhombuses, rounded-cornered rectangles (flat shapes), and spindle-like shapes enlarged (enlarged in diameter) at a central portion as compared with both end portions of the insertion portion being flat-shaped in cross section.

In accordance with an exemplary embodiment, such an operating member 7 can be configured to be higher than the puncture member 3 in rigidity. The material constituting the operating member 7 is not limited. Examples of the material applicable here can include various metallic materials such as stainless steels, aluminum, aluminum alloys, titanium, and titanium alloys.

The puncture member 3 is a member puncturing a living body. Such a puncture member 3 can include, for example, an elongate sheath (medical tube) (not shown), and a needle body provided at a distal end of the sheath as described in U.S. Patent Publication Nos. 2015/0080644, which is incorporated herein by reference in its entirety. For example, the sheath main body (not shown) can be configured by use of an elongate tube, which is open at a distal end and a proximal end of the elongate tube. Such a sheath main body can have an internal space in which an implant main body can be inserted. In addition, the sheath main body can be in an arcuate curved shape, and can have a flat cross-sectional shape.

In accordance with an exemplary embodiment, for example, the puncture member 3 passes through the living body from one groin to the other groin. A sheath for introducing the sling into the living body can be connected at the distal end of the puncture member 3 which is protruded out of the living body. The sheath can be placed into the living body by moving in the opposite direction to the direction of introducing the puncture member 3.

The frame 2 turnably holds the operating member 7 on which the puncture member 3 is mounted. In addition, the frame 2 detachably fixes the insertion instrument 6. The frame 2 has a function of determining a puncture route for the needle body 35 at the time of puncturing of a biological tissue by the puncture member 3. For example, the frame 2 can determine a positional relationship between the puncture member 3, the urethral insertion member 4, and the vaginal insertion member 5 in such a manner that when a biological tissue is punctured by the puncture member 3, the needle body 35 can pass between the urethral insertion member 4 and the vaginal insertion member 5 without colliding against or striking any of the insertion members 4 and 5.

As shown in FIGS. 1-5, the frame 2 can include a bearing portion 21, a guide portion (holding portion) 22 guiding the puncture member 3, an interlock portion 23 interlocking the bearing portion 21 and the guide portion 22 to each other, and a fixing portion 24 to which the insertion instrument 6 is fixed.

The bearing portion 21 can be located on the proximal end in the puncture apparatus 1. The guide portion 22 can be located on the distal end in the puncture apparatus 1, and is disposed opposite to the bearing portion 21. As shown in FIGS. 1-5, the guide portion 22 is formed with a roughly C-shaped guide groove (not shown) accommodating the puncture member 3 and guiding the puncture member 3.

Figure 2:
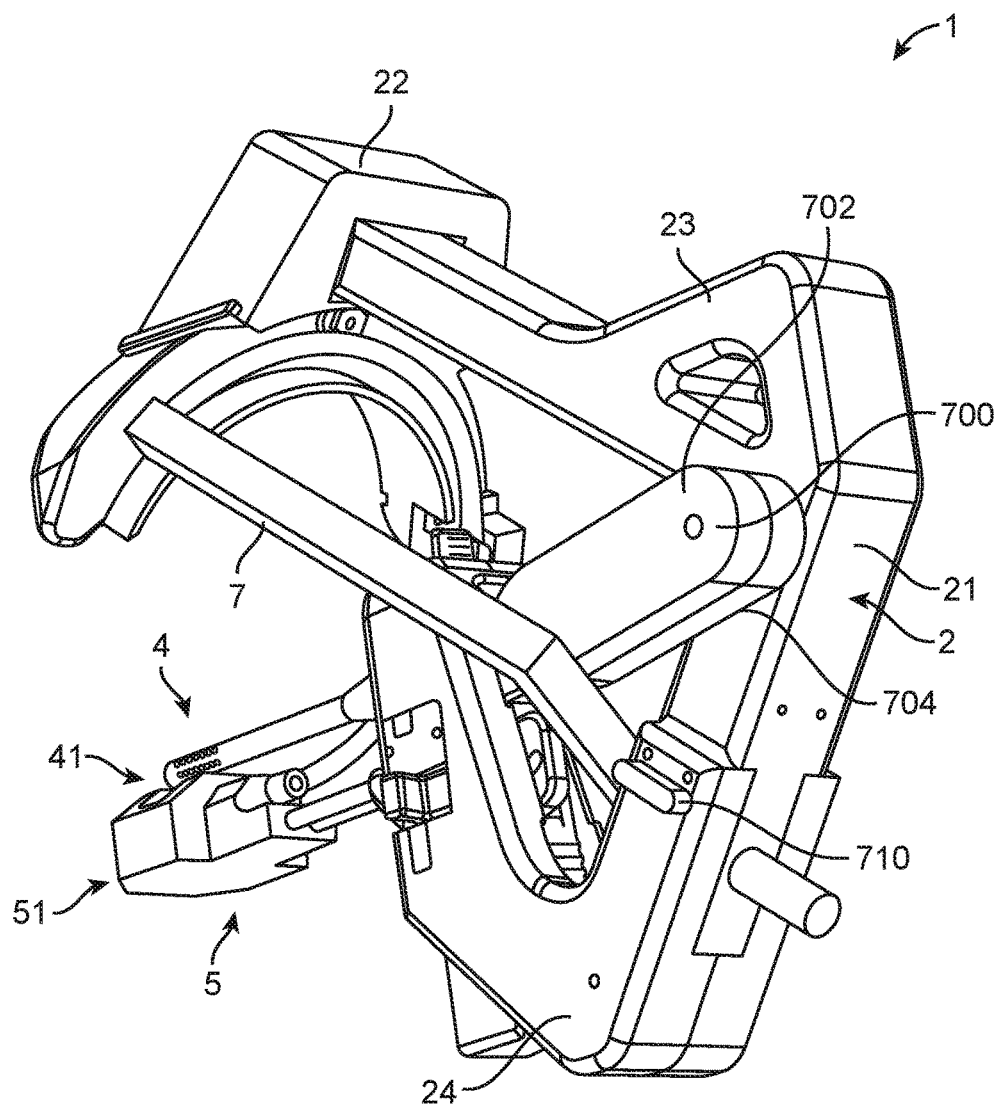
FIG. 2 is another perspective view showing a puncture apparatus to be used at a time of placing indwelling in a living body an implant according to an exemplary embodiment of the present disclosure.
Figure 3:
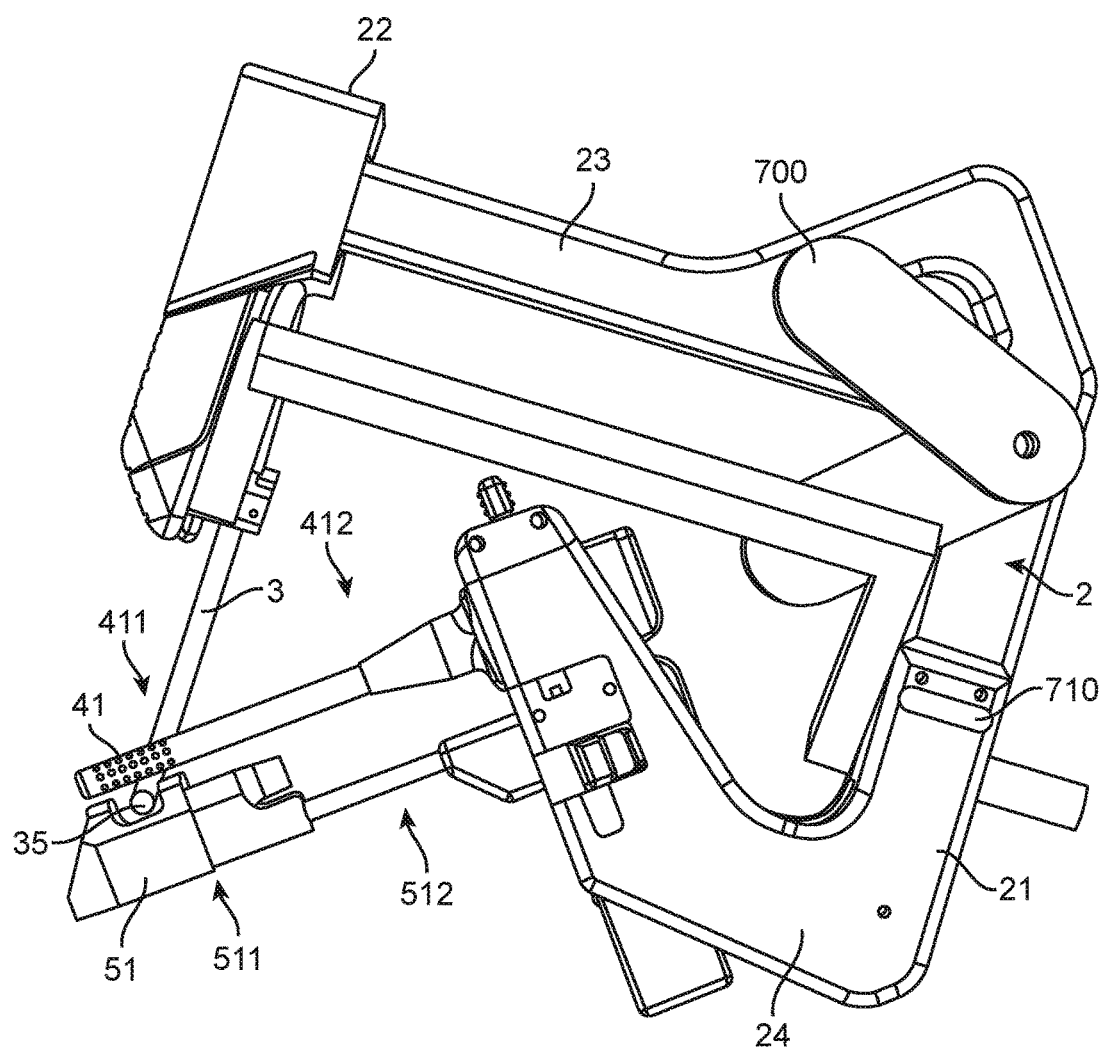
FIG. 3 is a perspective view showing a puncture apparatus to be used at a time of placing indwelling in a living body an implant according to an exemplary embodiment of the present disclosure.
Figure 4:
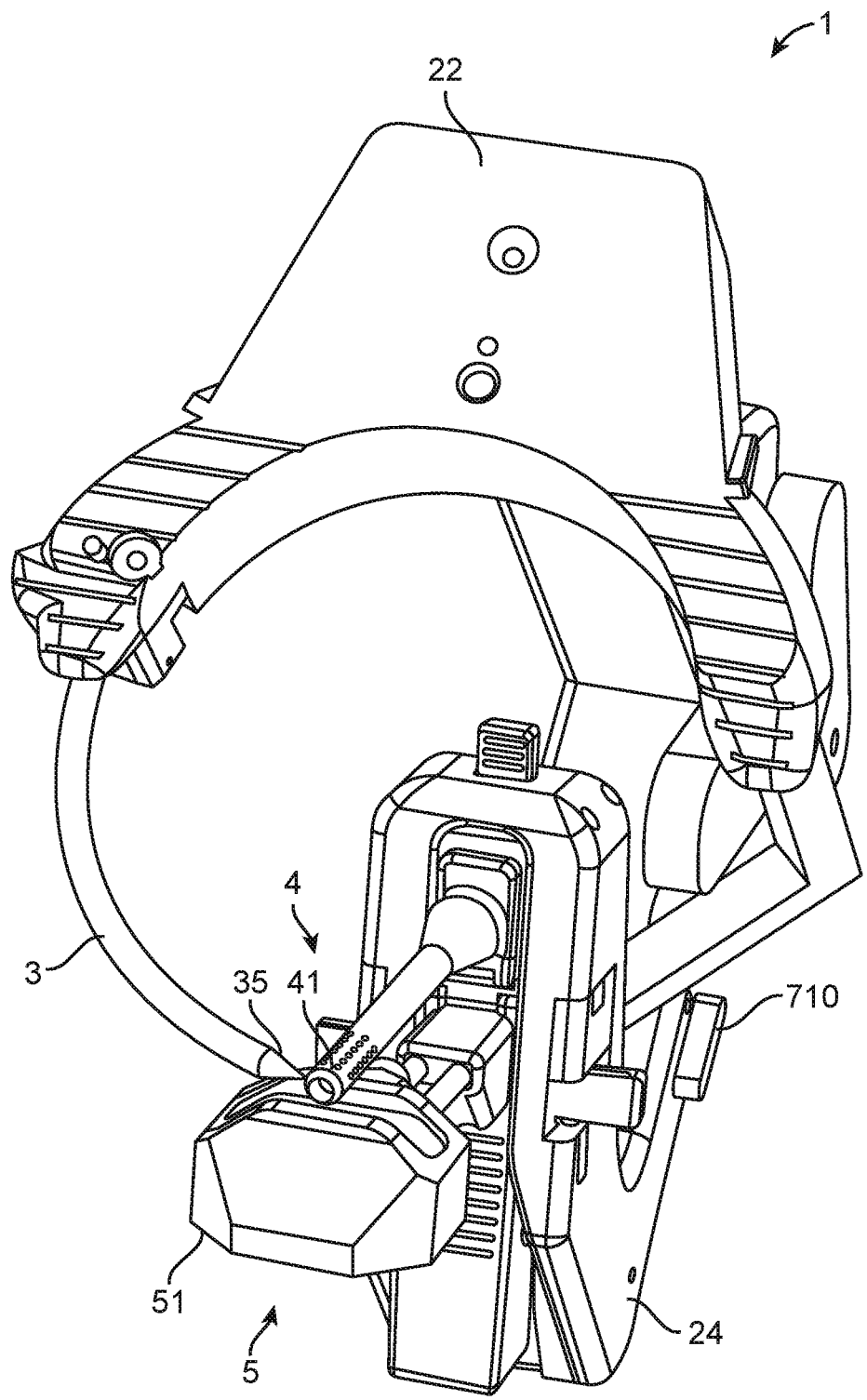
FIG. 4 is a perspective view showing a puncture apparatus to be used at a time of placing indwelling in a living body an implant according to an exemplary embodiment of the present disclosure.
Figure 5:
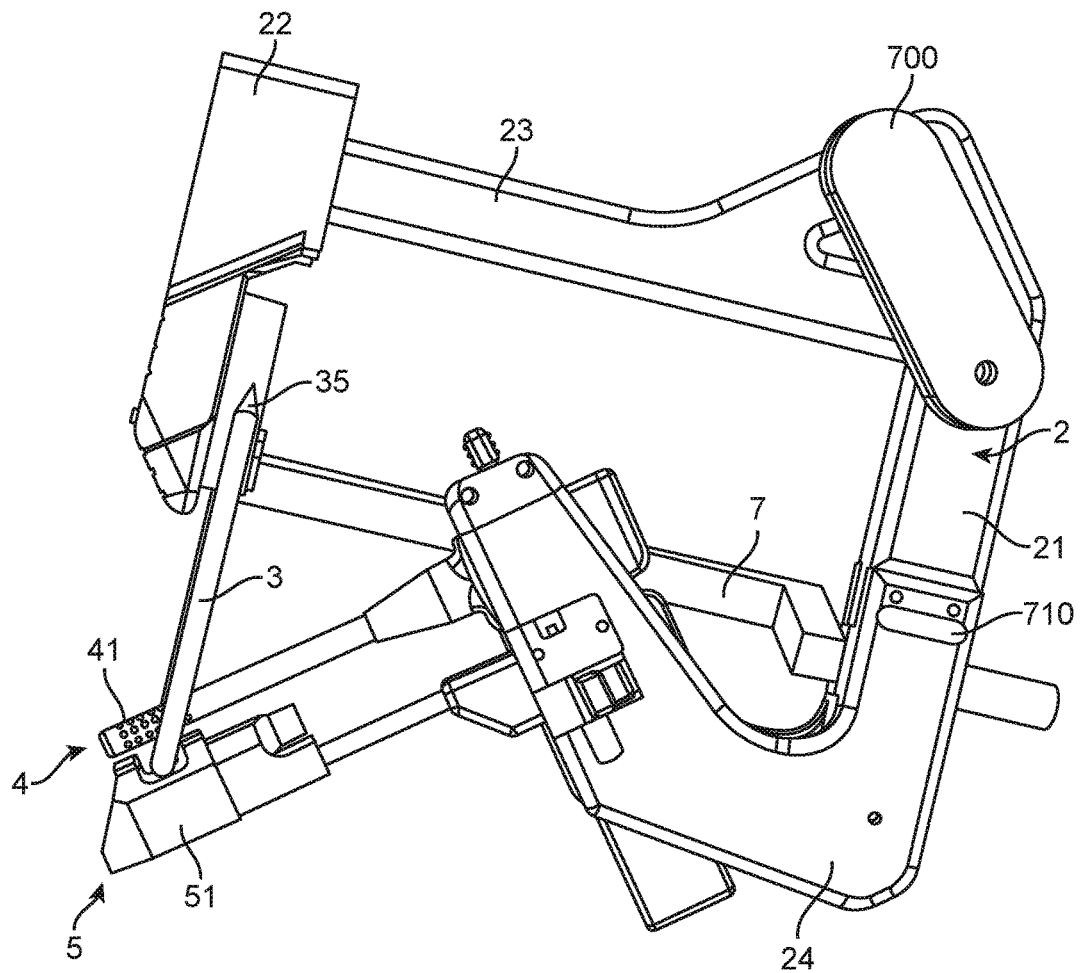
FIG. 5 is a perspective view showing a puncture apparatus to be used at a time of placing indwelling in a living body an implant according to an exemplary embodiment of the present disclosure.

When a rotating operation is applied to the operating member 7 as shown in FIGS. 2-5, the puncture member 3 gradually protrudes from the guide portion 22, and, the needle body 35 enters into the guide portion 22 via a proximal end opening. In accordance with an exemplary embodiment, the puncture apparatus 1 can include a stop plate (or needle stopper) 700, which can be used to control the movement of the puncture member 3 during use. In accordance with an exemplary embodiment, the stop plate 700 helps prevent the needle body 35 from piercing the puncture target until the stop plate 700 rotates upward as shown in FIGS. 1, 4, and 5, which allows the operating member 7 and the puncture member 3 to continue forward into and through the puncture target. In accordance with an exemplary embodiment, the stop plate 700 can be composed of at least a first part or section 702, and a second part of section 704, which are configured to overlap each other. (FIGS. 1 and 2). The first and second parts 702, 704 can move independently of each other, which allow the operator the ability to change the rotational distance of the operating member 7 based on which part or section 702, 704 of the stop plate 700 is used to stop the rotational movement of the operating member 7.

The apparatus 1 can also include an adjustment knob 710 (FIGS. 1-5 and 11). The adjustment knob 710 allows the operator to adjust the position of the fixing portion 24 in an up and down and forward and backward direction relative to the bearing portion 21, the guide portion 22, and the interlock portion 23. Thus, by adjusting the relative position of the fixing portion 24 to the bearing portion 21, the guide portion 22, and the interlock portion 23, the position of the urethral insertion member 4 and vaginal insertion member 5 relative to the puncture member 3 can be changed and adjusted as needed.

The interlock portion 23 can interlock the shaft portion 21 and the guide portion 22 to each other. In addition, the interlock portion 23 can be in the shape of a bar. The interlock portion 23 can also function as a grasping portion, allowing an operator to use the puncture apparatus 1 while grasping the interlock portion 23.

As shown in FIGS. 1-5, the insertion instrument 6, which can include a urethral insertion member (second insertion portion) 41 to be inserted into a urethra, a vaginal insertion member (first insertion portion) 51 to be inserted into a vagina, and a support portion 60 supporting the urethral insertion portion 41 and the vaginal insertion portion 51. As disclosed above, the insertion instrument 6 can be composed essentially of the urethral insertion member 4 and the vaginal insertion member 5. The urethral insertion member 4 can have the urethral insertion portion 41, and the vaginal insertion member 5 has the vaginal insertion portion 51.

In addition, the support portion 60 can include a support portion 40, which is possessed by the urethral insertion member 4 and supports the urethral insertion portion 41, and a support portion 50, which is possessed by the vaginal insertion member 5 and supports the vaginal insertion portion 51. In the insertion instrument 6, the urethral insertion member 4 and the vaginal insertion member 5 can be freely detachable by way of the support portions 40 and 50, respectively. The urethral insertion member 4 and the vaginal insertion member 5 will be sequentially described below.

As shown in FIGS. 1-5, the urethral insertion member 4 can include the elongated urethral insertion portion 41 whose portion ranging from a distal end to an intermediate portion of insertion member 41 is to be inserted into a urethra, and the support portion 40, which supports the urethral insertion portion 41. In the following, for convenience of description as shown in FIG. 3, that portion of the urethral insertion member 4 which is located inside the urethra (inclusive of a bladder) in the mounted state will be referred to also as "insertion portion 411," whereas that portion of the urethral insertion member 4 which is exposed via a urethra orifice to the outside of the body in the mounted state and which ranges to the support portion 40 will be referred to also as "non-insertion portion 412."

The vaginal insertion member 5 can include the elongated vaginal insertion member (first insertion portion) 51 whose portion from a distal end to an intermediate portion of insertion member 51 is inserted into a vagina, and the support portion 50 supporting the vaginal insertion portion 51. In the following, for convenience of description as shown in FIG. 3, that portion which is located in the vagina in the mounted state will be referred to also as the "insertion portion 511," and that portion which is exposed via a vaginal orifice to the outside of the body in the mounted state and which ranges to the support portion 50 will be referred to also as "non-insertion portion 512."

The vaginal insertion portion 51 can be elongated. In accordance with an exemplary embodiment, the vaginal insertion portion 511 is spaced from the urethral insertion portion 411 on the distal end. In accordance with an exemplary embodiment, the vaginal insertion portion 511 can be parallel or inclined relative to the urethral insertion portion 411. In the mounted state, for example, the puncture apparatus 1 can be held stably onto the patient, and burden on the patient can be mitigated. The inclination angle of the insertion portion 511 relative to the insertion portion 411 is not limited, for example, the inclination angle can be about 0 to 45 degrees, and more preferably about 0 to 30 degrees, or alternatively, most preferably about 0 degrees as shown in FIGS. 6-10.

Figure 6:
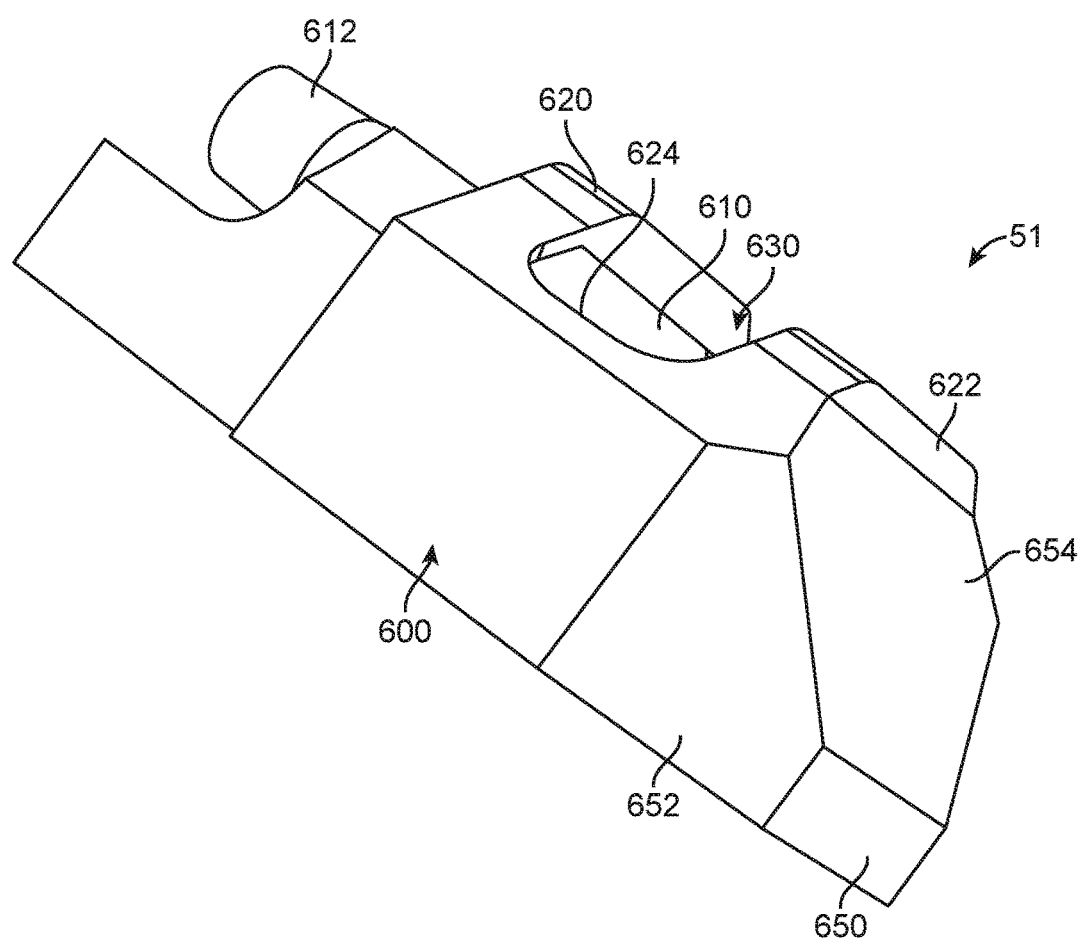
FIG. 6 is a perspective view showing a vaginal insertion portion according to an exemplary embodiment.
Figure 8:
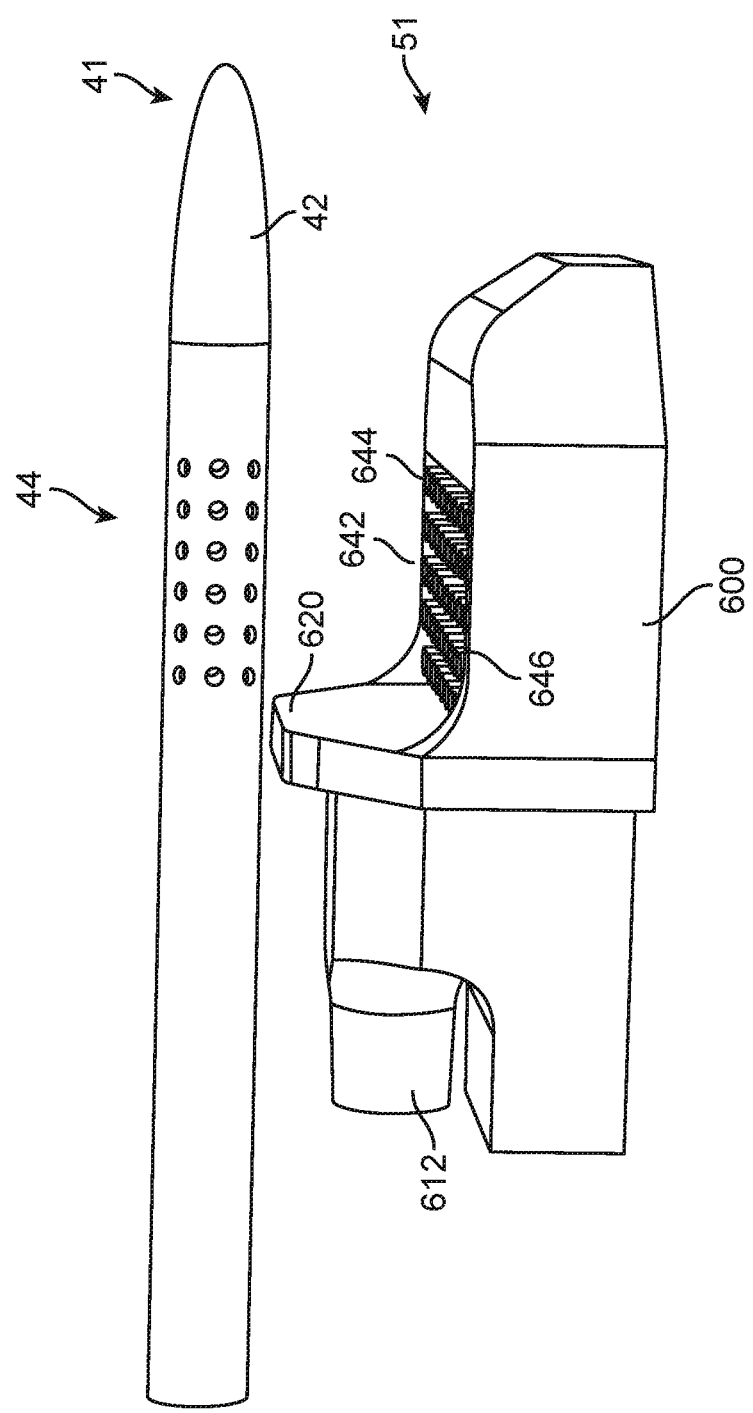
FIG. 8 is a perspective view showing a urethral insertion portion and a vaginal insertion portion according to another exemplary embodiment.

As shown in FIG. 6, the vaginal insertion portion 51 of the vaginal insertion member 5 can include a relatively flat base portion 600, a suction portion 610, a proximal portion (or proximal holding portion) 620, a distal portion (or distal holding portion) 622, and a pair of sidewalls 624. As shown in FIG. 6, the vaginal insertion portion 51 of the vaginal insertion member 5 is configured to hold the puncture target in a one-to-one ratio and includes a needle pass portion 630. The needle pass portion 630 is located above the suction portion 610 and to a distal side of the proximal holding portion 620. In accordance with an exemplary embodiment, the distal holding portion 622 is located on a distal side of the needle pass portion 630. The pair of sidewalls 624 can have a height less than the height of the proximal portion 620 and the optional distal portion 622, such that the needle pass portion 630 can be formed. The pair of sidewalls 624 is optional and can be omitted, for example, as shown in FIG. 8.

In accordance with an exemplary embodiment, a distal portion of the vaginal insertion portion 51 includes a distal end 650, a pair of angled sidewalls 652 extending from the distal end 650 and an angled upper surface 654 extending towards the distal portion 622 and the suction portion 610.

The vaginal insertion portion 51 can also include a suction port 612 on the proximal portion, which is communication with the suction portion 610 of the vaginal insertion portion 51. The suction port 612 can be connected to a suction device, such as a pump, and when the suction device is operated in a state wherein the vaginal insertion portion 51 is inserted in the vagina, a vaginal wall can be sucked and fixed onto the suction portion 610.

In accordance with an exemplary embodiment, a distance from the proximal holding portion 620 to the distal holding portion 622 can be, for example, about 5 mm to 30 mm, and more preferably about 8 mm to 18 mm. For example, the suction portion 610 can have a length of about 5 mm to 30 mm, and more preferably about 10 to 20 mm, and a width of about 5 mm to 60 mm, and more preferably about 25 mm to 50 mm. In accordance with an exemplary embodiment, the needle pass portion 630 preferably has a height of 3 mm to 20 mm, a width of 7 mm to 62 mm, and a length of 5 mm to 30 mm.

The vaginal insertion portion 51 of can have a substantially constant width and a somewhat rounded and angled distal portion. For example, a length of the vaginal insertion portion 51 is not limited, and can be, for example, about 20 to 100 mm, more preferably about 30 to 60 mm. A width of the vaginal insertion portion 51 is not limited, and can be, for example, about 10 to 60 mm, more preferably about 30 to 50 mm. In addition, the thickness of the vaginal insertion portion 51 is not limited, and can be, for example, about 5 to 35 mm, more preferably about 15 to 25 mm. Set to have such length, width, and thickness, the vaginal insertion portion 51 is suited in shape and size to ordinary vaginas. Therefore, stability of the puncture apparatus 1 in the mounted state can be enhanced, and burden on the patient can be relatively alleviated.

The material constituting the vaginal insertion member 5 is not limited. Examples of the material applicable here include various metallic materials such as stainless steels, aluminum, aluminum alloys, titanium, titanium alloys, etc.

and various resin materials, like the examples of the material for the urethral insertion member 4.

Figure 7:
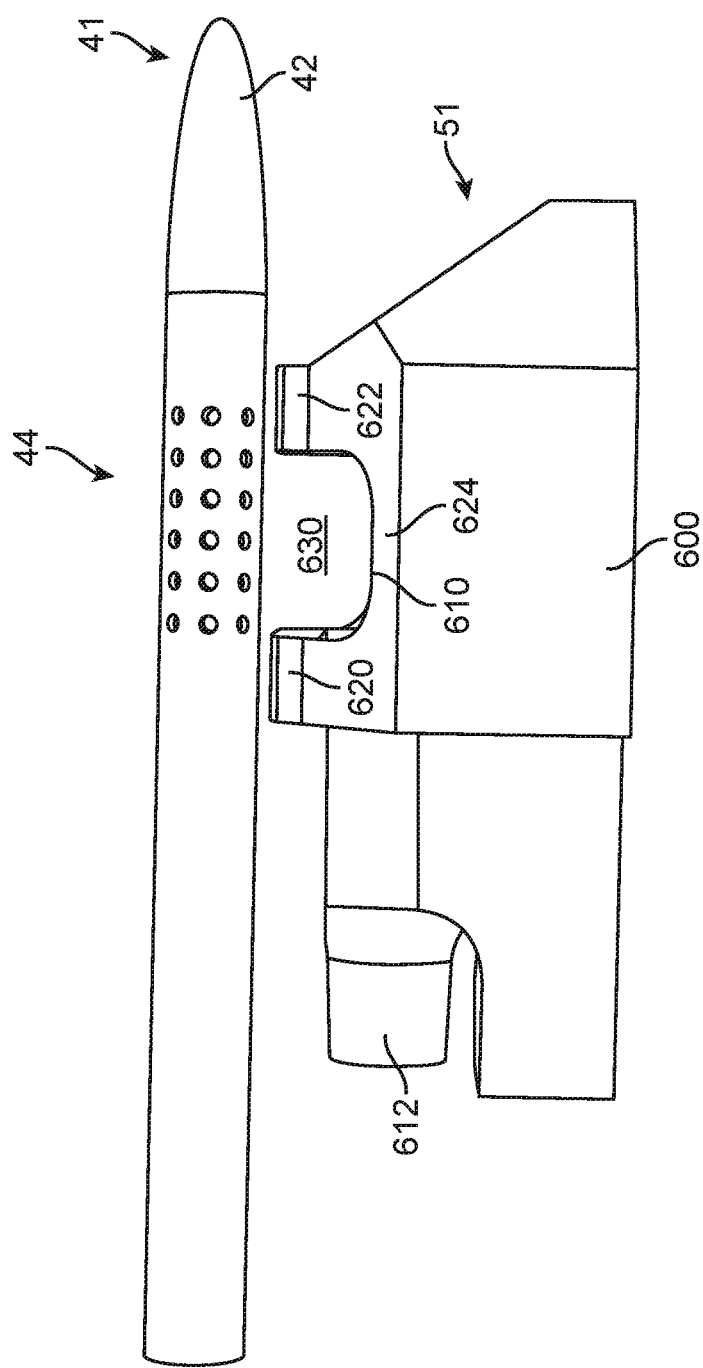
FIG. 7 is a perspective view showing a urethral insertion portion and a vaginal insertion portion according to an exemplary embodiment.

FIG. 7 is a side view showing a urethral insertion member 4 and a vaginal insertion member 5 according to an exemplary embodiment. As shown in FIG. 7, the urethral insertion member 4 can include the elongated urethral insertion portion 41 whose portion ranging from a distal end to an intermediate portion of insertion member 41 is to be inserted into a urethra, and the support portion 40, which supports the urethral insertion portion 41.

The urethral insertion portion 41 can be in the shape of a tube with its distal end rounded. In addition, the insertion portion 411 is provided at its distal portion with an inflatable and deflatable balloon 42 and a urine drain portion (not shown). The balloon 42 can function as a restriction portion restricting the position in an axial direction of the urethral insertion member 4 in the inside of the urethra. For example, when the puncture apparatus 1 is used, the balloon 42 is inflated after inserted into a patient's bladder. Then, with the balloon 42 caught on a bladder neck, the position of the urethral insertion member 4 relative to the bladder and the urethra is fixed. In accordance with an exemplary embodiment, the urine drain portion can be used for draining urine present inside the bladder.

The balloon 42 extends through the inside of the urethral insertion portion 41, to be connected to a balloon port (not shown) provided at a proximal portion of the urethral insertion portion 41. A balloon-inflating instrument such as a syringe can be connected to the balloon port (not shown). When a working fluid (a liquid such as physiological salt solution, or a gas or the like) is supplied from the balloon-inflating instrument into the balloon 42, the balloon 42 is inflated. When the working fluid is drawn out of the balloon 42 by the balloon-inflating instrument, the balloon 42 is deflated. The balloon 42 and the urine drain portion (not shown) can be configured by use of a double lumen, for example.

In addition, the insertion portion 411 can be formed with a plurality of suction holes 44 at an intermediate portion of the insertion portion 411. The plurality of suction holes 44 can be laid out over the whole range in the circumferential direction of the urethral insertion portion 41. Each of the suction holes 44 can be connected to a suction port 45 provided at a proximal portion of the urethral insertion portion 41, via the inside of the urethral insertion portion 41. A suction device such as a pump can be connected to the suction port (not shown). When the suction device is operated in a state wherein the urethral insertion portion 41 is inserted in the urethra, a urethral wall can be sucked and fixed onto the urethral insertion portion 41. When the urethral insertion portion 41 is pushed in toward the distal end (toward the inside of the body) under this condition, the urethra is also pushed in together with the urethral insertion portion 41. As a result, for example, the bladder and the urethra can be shifted to such a position as not to overlap with a puncture route for the puncture member 3, whereby the puncture route for the puncture member 3 can be secured. Therefore, puncturing by the puncture member 3 can be carried out relatively accurately and safely. It is to be noted that the number of the suction holes 44 is not limited, for example, the number may be one. In addition, layout of the suction holes 44 is not limited, for example, the suction holes 44 may be formed in only a part of the range in the circumferential direction of the urethral insertion portion 41.

In addition, at the boundary portion between the insertion portion 411 and the non-insertion portion 412, a marker (not shown) can be provided to check the depth of insertion of the urethral insertion portion 41 into the urethra. When the urethral insertion portion 41 is inserted in the urethra and the balloon 42 is located inside the bladder, the marker is located at the urethral orifice, which permits relatively easy checking of the depth of insertion of the insertion portion 411 into the urethra. The marker is necessary only to be externally visible, and can be composed essentially of, for example, a colored portion, a recessed and projected portion, or the like. In accordance with an exemplary embodiment, a graduation with indications of distance from the distal end of the urethral insertion portion 41 may be provided, in place of the marker.

The length of the insertion portion 411 is not limited, and may be set, as necessary, according to the length of the urethra and the shape of the bladder of the patient, or the like. The length of the insertion portion 411 can be, for example, about 50 to 100 mm, in view of the fact that the length of a female urethra is generally about 30 to 50 mm.

The length of the non-insertion portion 412 (the spacing between the urethral orifice and the support portion 40) is not limited. The length can be, for example, not more than about 100 mm, preferably in the range of about 20 to 50 mm. By such a setting, the length of the non-insertion portion 412 can be made appropriate, which can provide relatively enhanced operability. For example, if the length of the non-insertion portion 412 exceeds the just-mentioned upper limit, the center of gravity of the puncture apparatus 1 would, depending on the configuration of the frame 2 or the like factors, be largely deviated from the patient, possibly leading to a lowered stability of the puncture apparatus 1 in the mounted state.

The material constituting the urethral insertion member 4 is not limited. Examples of the material applicable here include various metallic materials such as stainless steels, aluminum, aluminum alloys, titanium, titanium alloys, etc. and various resin materials.

FIG. 8 is a side view showing a urethral insertion portion 41 and a vaginal insertion portion 51 according to another exemplary embodiment. As shown in FIG. 8, the vaginal insertion member can include a proximal holding portion 620 and a suction portion 610. The distal holding portion 622 and the pair of sidewalls 624 can be optional and are not necessary. As shown in FIG. 8, on an upper surface 642 of the suction portion 610 of the vaginal insertion portion 51 can be formed with a plurality of bottomed recesses 644. The number of the recesses 644 is not limited, for example, the number may be one. In addition, each recess 644 can be provided with at least one suction hole 646 in its bottom surface. Each suction hole 646 is connected to a suction port 612 provided at a proximal portion of the insertion portion 511, through the inside of the insertion portion 511. The suction port 612 is preferably provided so as to be located outside of the living body in the mounted state. A suction device such as a pump can be connected to the suction port. When the suction device is operated in the condition where the insertion portion 511 is inserted in a vagina, an anterior wall of vagina, which is an upper surface of a vaginal wall, is sucked and fixed onto the suction portion 610. When the vaginal insertion portion 51 with the vaginal wall sucked and fixed thereon is pushed toward the distal end (toward the inside of the body), the vaginal wall can be pushed in together with the vaginal insertion portion 51. Therefore, it is possible to put in good order the configuration and shape of the vaginal wall, to secure a puncture route for the puncture member 3, and to perform puncturing by the puncture member 3 relatively accurately and safely.

Figure 9:
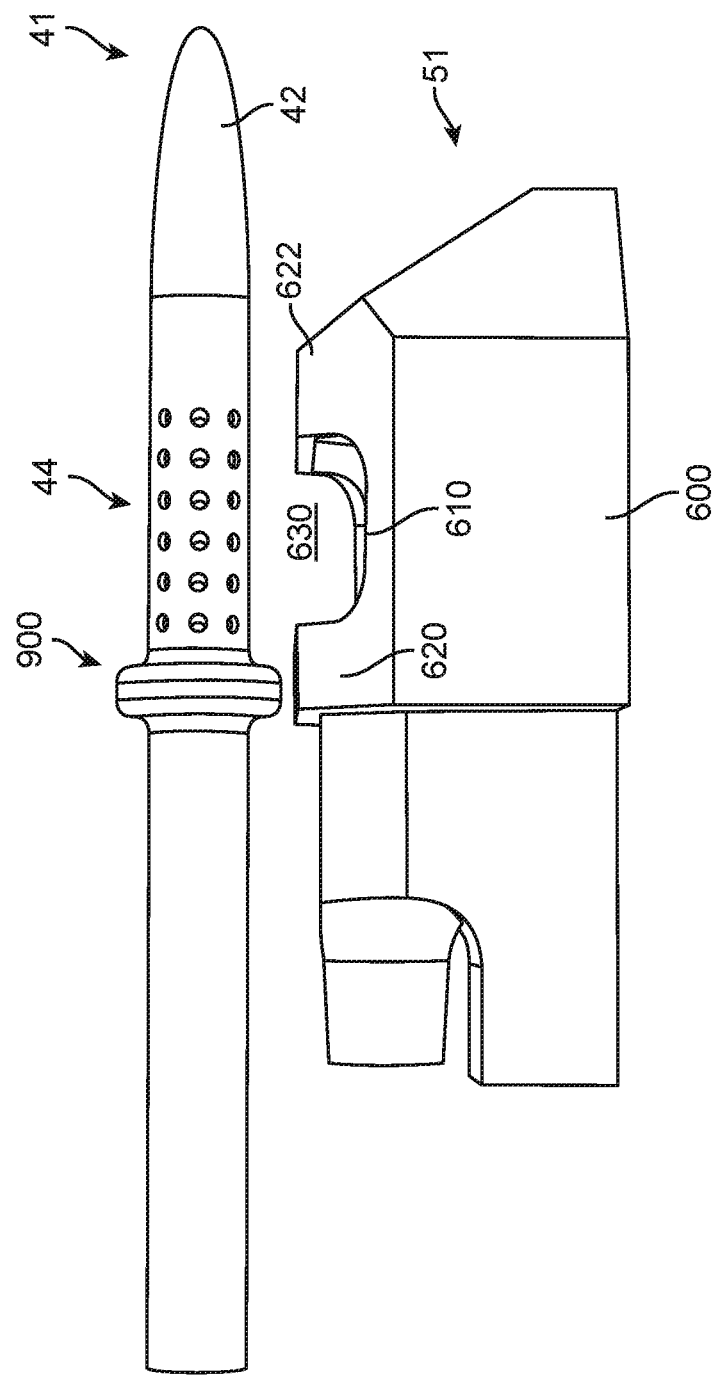
FIG. 9 is a perspective view showing a urethral insertion portion and a vaginal insertion portion according to an exemplary embodiment.

FIG. 9 is a perspective view showing a urethral insertion portion 41 and a vaginal insertion portion 51 according to an exemplary embodiment. As shown in FIG. 9, the vaginal insertion portion 51 can include a relatively flat base portion 600, a suction portion 610, proximal holding portion 620, a distal holding portion 622, and a pair of sidewalls 624. The insertion portion 511 of the vaginal insertion member 5 is configured to hold the puncture target in a one-to-one ratio and includes a needle pass portion 630. The needle pass portion 630 is located above the suction portion 610 and to a distal side of the proximal holding portion 620. In accordance with an exemplary embodiment, the proximal portion 622 is located on a proximal side of the needle pass portion 630.

In addition, as shown in FIG. 9, the urethral insertion member 4 can include a collar 900 formed on a proximal side of the plurality of suction holes 44 of the urethral insertion portion 41. The collar 900 can be configured to be positioned above the proximal portion 620 of the vaginal insertion portion 51.

Figure 10:
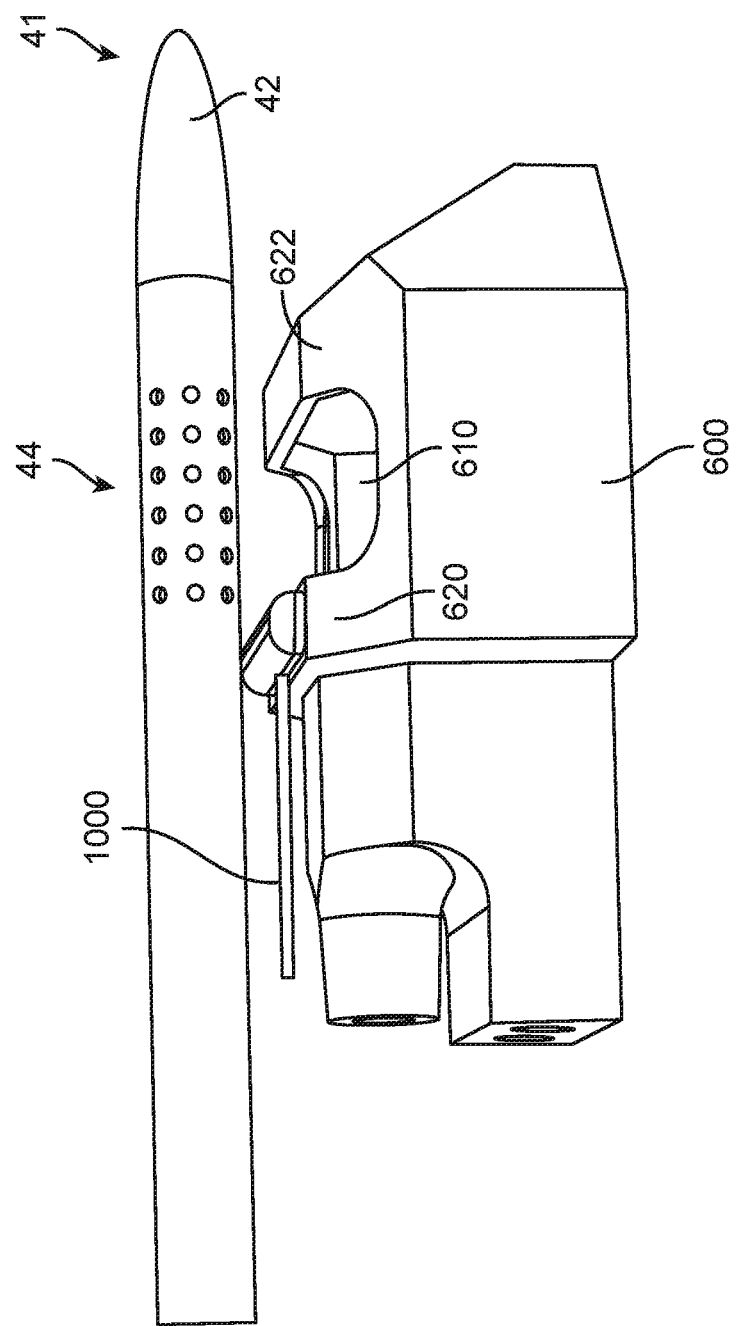
FIG. 10 is a perspective view showing a urethral insertion portion and a vaginal insertion portion according to an exemplary embodiment.

FIG. 10 is a perspective view showing a urethral insertion portion 41 and a vaginal insertion portion 51 according to an exemplary embodiment. As shown in FIG. 10, the vaginal insertion portion 51 can include a proximal balloon 1000. In accordance with an exemplary embodiment, the proximal balloon 1000 is positioned on a proximal side of the proximal portion of the vaginal insertion portion 51. In use, the proximal balloon 1000 functions as a restriction portion restricting the position in an axial direction of the vaginal insertion portion 51. A balloon-inflating instrument such as a syringe can be connected to the balloon port (not shown). When a working fluid (a liquid such as physiological salt solution, or a gas or the like) is supplied from the balloon-inflating instrument into the balloon 1000, the balloon 1000 is inflated. When the working fluid is drawn out of the balloon 1000 by the balloon-inflating instrument, the balloon 1000 is deflated.

Figure 11:
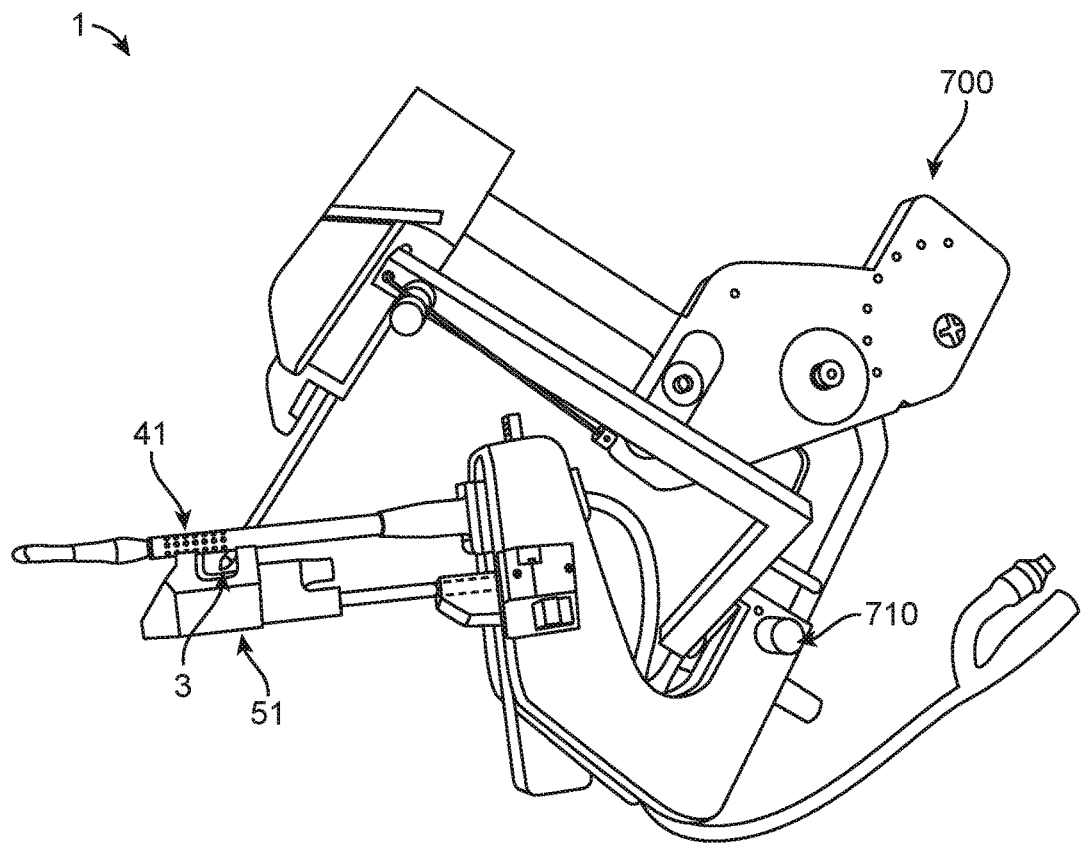
FIG. 11 is a perspective view showing a puncture apparatus to be used at a time of placing indwelling in a living body an implant according to an exemplary embodiment of the present disclosure.

FIG. 11 is a perspective view showing a puncture apparatus 1 to be used at a time of placing indwelling in a living body an implant according to an exemplary embodiment of the present disclosure. As shown in FIG. 11, the puncture apparatus 1 can include a frame (support unit) 2, a puncture member 3 having a needle body 35, a urethral insertion member 4 having a urethral insertion portion 41, a vaginal insertion member 5 having a vaginal insertion portion 51, and an operating member 7. The apparatus 1 can also include a stop plate (or needle stopper) 700 and an adjustment knob 710. The adjustment knob 710 allows the operator to adjust the position of the urethral insertion member 4 and vaginal insertion member 5 relative to the puncture member 3.

Figure 12A:
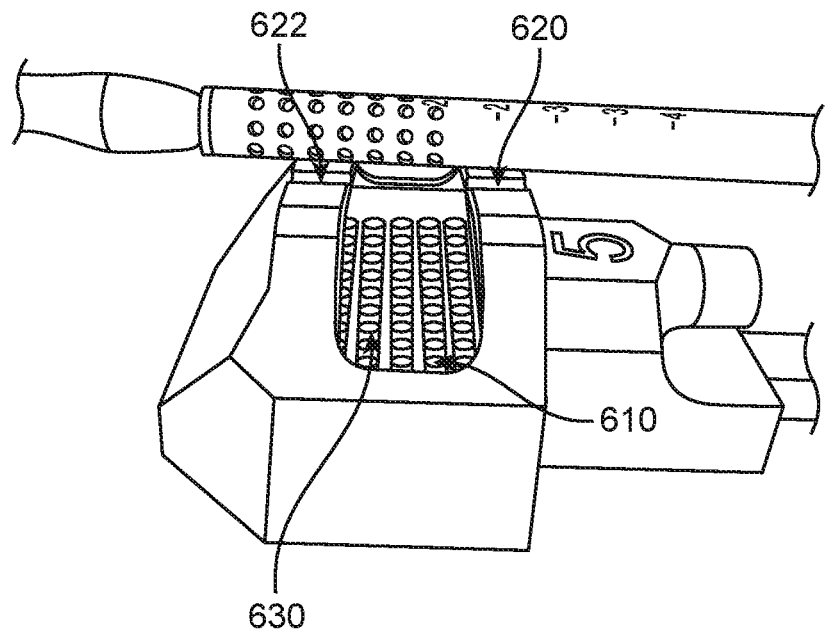
FIG. 12A is a perspective view showing a vaginal stabilizer and a urethral stabilizer according to an exemplary embodiment.
Figure 12B:
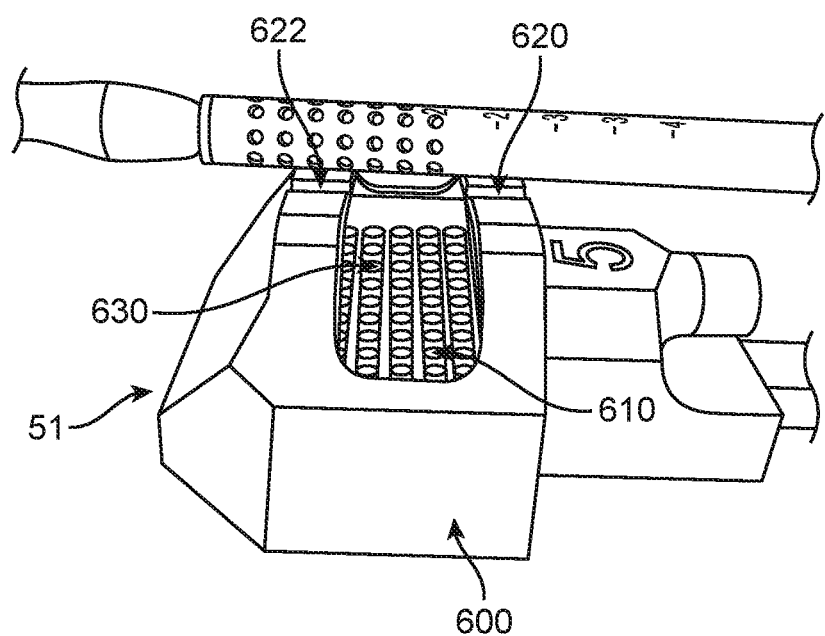
FIG. 12B is a perspective view showing a vaginal stabilizer and a urethral stabilizer according to an exemplary embodiment.

FIG. 12A is a perspective view showing the vaginal insertion portion 51 and a urethral insertion portion 41 according to an exemplary embodiment. As shown in FIG. 12A, the vaginal insertion portion 51 including a proximal holding portion 620, a distal holding portion 622, and a suction portion 610. FIG. 12B is a perspective view showing the needle pass portion 630 of the vaginal insertion portion 51.

Figure 13:
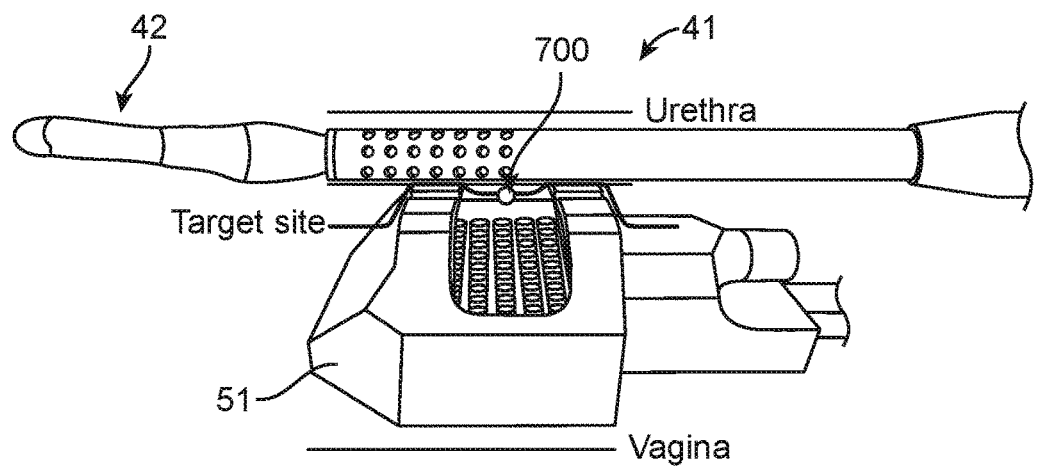
FIG. 13 is a perspective view showing a vaginal stabilizer and a urethral stabilizer with the suction off according to an exemplary embodiment.

FIG. 13 is a perspective view showing the vaginal insertion portion 51 and the urethral insertion portion 41 with the suction off according to an exemplary embodiment. As shown in FIG. 13, with the suction off, the target site 700 rests freely within the needle pass portion 630.

Figure 14:
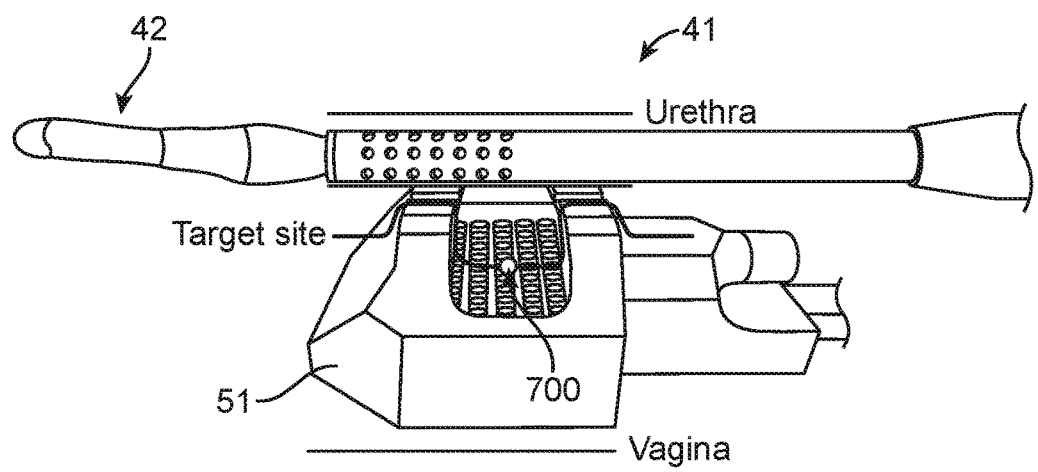
FIG. 14 is a perspective view showing a vaginal stabilizer and a urethral stabilizer with the suction on according to an exemplary embodiment.

FIG. 14 is a perspective view showing the vaginal insertion portion 51 and the urethral insertion portion 41 with the suction on according to an exemplary embodiment. As shown in FIG. 14, with the suction on, the needle tip of the puncture member can pass through the needle pass portion 630 and between the vaginal insertion portion 51 and the urethral insertion portion 41 into the target site 700. As shown, a lower surface of the urethral wall is sucked onto the insertion portion 51 and the anterior wall of vagina is sucked onto the suction portion 610, as disclosed above, the urethral wall and the vaginal wall are spaced wider apart from each other By causing the puncture member 3 to pass through the needle pass portion 630 as disclosed herein, the puncturing of the target site 700 by the puncture member 3 can be performed relatively safely.

In addition, while the case where the puncture apparatus 1 is applied to an implant for treatment of female urinary incontinence has been described in the above exemplary embodiments, this is not restrictive of the use of the implant.

Examples of which the present disclosure is applicable can include pelvic floor diseases inclusive of excretory disorders (urinary urgency, frequent urination, urinary incontinence, fecal incontinence, urinary retention, dysuria, etc.), pelvic organ prolapse, vesicovaginal fistula, urethrovaginal fistula, and pelvic pain, which would be attendant on weakening of the group of pelvic floor muscles. The pelvic organ prolapse include such diseases as cystocele, enterocele, rectocele, and hysterocele, or such diseases as anterior vaginal prolapse, posterior vaginal prolapse, vaginal apical prolapse, and vaginal vault prolapse, which are denominations based on classification of the vaginal wall part being prolapsed.

In addition, examples of overactive tissue can include the bladder, vagina, uterus, and bowels. Examples of lessactive tissue can include bones, muscles, fascias, and ligaments. For example, in relation to the pelvic floor diseases, examples of the lessactive tissue include obturator fascia, coccygeus fascia, cardinal ligament, uterosacral ligament, and sacrospinous ligament.

Examples of the procedure for interlocking an overactive tissue in the pelvic floor disorder with the lessactive tissue, can include a retropubic sling surgery, a transobturator sling surgery (Transobturator Sling Surgery, Transobturator Tape; TOT), a tension-free vaginal mesh (Tension-free Vaginal Mesh; TVM) surgery, a uterosacral ligament suspension (Uterosacral Ligament Suspension; USLS) surgery, an iliococcygeus fascia fixation surgery, and a coccygeus fascia fixation surgery.

The detailed description above describes a puncture apparatus. The disclosure is not limited, however, to the precise exemplary embodiments and variations described. Various changes, modifications and equivalents can effected by one skilled in the art without departing from the spirit and scope of the disclosure as defined in the accompanying claims. It is expressly intended that all such changes, modifications, and equivalents which fall within the scope of the claims are embraced by the claims.

What is claimed is:
1. A puncture apparatus comprising:
an insertion portion that is insertable into a living body, the insertion portion comprising:
a urethral insertion portion having an inflatable and deflatable balloon on a distal end of the urethral insertion portion, and a plurality of suction holes at an intermediate portion of the urethral insertion portion; and
a vaginal insertion portion, the vaginal insertion portion having a base portion, a proximal holding portion located on a proximal side of the base portion, and a suction portion located distally of the proximal hold- ing portion and configured to suck an anterior wall of a target site onto the suction portion;

a needle pass portion, the needle pass portion located above the suction portion and to a distal side of the proximal holding portion; and a puncture needle configured to pass through the needle pass portion and puncture living body tissues between the urethral insertion portion and the vaginal insertion portion in a state in which the insertion portion is inserted into the living body.

2. The puncture apparatus of claim 1, wherein the vaginal insertion portion comprises:
a distal holding portion located distally of the suction portion.

3. The puncture apparatus of claim 1, wherein the base portion of the vaginal insertion portion is relatively flat.

4. The puncture apparatus of claim 1, wherein the suction portion of the vaginal insertion portion comprises:
a plurality of recesses, each of the plurality of recesses configured to be connected with a suction hole, and wherein each suction hole is connected to a suction port.

5. The puncture apparatus of claim 1, wherein a distal portion of the vaginal insertion portion includes a distal end, a pair of angled sidewalls extending from the distal end and an angled upper surface extending towards the suction portion.

6. The puncture apparatus of claim 1, comprising:
a collar on the urethral insertion portion, the collar being proximal to the plurality of suction holes.

7. The puncture apparatus of claim 1, wherein the vaginal insertion portion includes a balloon, the balloon being proximal to the proximal holding portion of the vaginal insertion portion.

8. The puncture apparatus of claim 1, wherein the plurality of suction holes at the intermediate portion of the urethral insertion portion are located proximally and adjacent to the deflatable balloon on the distal end of the urethral insertion portion.

9. A method for puncturing a tissue of a living body, comprising:

inserting an insertion portion into the living body, the insertion portion comprising a urethral insertion portion, a vaginal insertion portion, and a needle pass portion, the urethral insertion portion having an inflatable and deflatable balloon on a distal end of the urethral insertion portion, and a plurality of suction holes at an intermediate portion of the urethral insertion portion, the vaginal insertion portion having a base portion, a proximal holding portion located on a proximal side of the base portion, and a suction portion located distally of the proximal holding portion, and the needle pass portion being located above the suction portion and to a distal side of the proximal holding portion and configured to allow a puncture needle to pass through the needle pass portion and puncture the tissue;

applying a suction to the suction portion so that the insertion portion suctions an anterior wall of a target site onto the suction portion; and passing a puncture needle through the needle pass portion and puncturing the tissue of the living body between the urethral insertion portion and the vaginal insertion portion.

10. The method of claim 9, wherein the vaginal insertion portion comprises:
a distal holding portion located on distal side of the suction portion.

11. The method of claim 9, wherein the suction portion of the vaginal insertion portion comprises:
a plurality of recesses, each of the plurality of recesses configured to be connected with a suction hole, and wherein each suction hole is connected to a suction port; and
a distal portion of the vaginal insertion portion includes a distal end, a pair of angled sidewalls extending from the distal end and an angled upper surface extending towards the suction portion.

12. The method of claim 9, comprising:
a collar on the urethral insertion portion, the collar being proximal to the plurality of suction holes.

* * * * *